(12) United States Patent
Alkhatib et al.

(10) Patent No.: US 8,932,343 B2
(45) Date of Patent: *Jan. 13, 2015

(54) BLUNT ENDED STENT FOR PROSTHETIC HEART VALVE

(75) Inventors: Yousef F. Alkhatib, Edina, MN (US); Peter Nicholas Braido, Wyoming, MN (US); Thomas M. Benson, Minneapolis, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 35 days.

This patent is subject to a terminal disclaimer.

(21) Appl. No.: 13/215,893

(22) Filed: Aug. 23, 2011

(65) Prior Publication Data
US 2012/0197390 A1 Aug. 2, 2012

Related U.S. Application Data
(60) Provisional application No. 61/438,451, filed on Feb. 1, 2011.

(51) Int. Cl.
*A61F 2/24* (2006.01)
*A61F 2/95* (2013.01)

(52) U.S. Cl.
CPC ............ *A61F 2/2418* (2013.01); *A61F 2/2436* (2013.01); *A61F 2220/0075* (2013.01); *A61F 2002/9517* (2013.01); *A61F 2002/9534* (2013.01); *A61F 2250/0039* (2013.01)
USPC ....... 623/1.24; 623/1.15; 623/1.26; 623/2.14; 623/2.17; 623/2.18

(58) Field of Classification Search
USPC ............... 623/1.24, 1.26, 2.14, 2.17, 1.15
See application file for complete search history.

(56) References Cited

U.S. PATENT DOCUMENTS

| | | |
|---|---|---|
| 3,657,744 A | 4/1972 | Ersek |
| 4,275,469 A | 6/1981 | Gabbay |
| 4,491,986 A | 1/1985 | Gabbay |
| 4,759,758 A | 7/1988 | Gabbay |
| 4,922,905 A | 5/1990 | Strecker |
| 5,391,172 A | 2/1995 | Williams et al. |
| 5,411,552 A | 5/1995 | Andersen et al. |
| 5,456,667 A | 10/1995 | Ham et al. |
| 5,480,423 A | 1/1996 | Ravenscroft et al. |
| 5,843,167 A | 12/1998 | Dwyer et al. |
| 5,935,163 A | 8/1999 | Gabbay |

(Continued)

FOREIGN PATENT DOCUMENTS

| WO | WO 2009029199 A1 * | 3/2009 | ............... A61F 2/24 |
|---|---|---|---|
| WO | 2009/042196 A2 | 4/2009 | |

OTHER PUBLICATIONS
International Search Report Application No. PCT/US2011/048963, dated Dec. 15, 2011.

(Continued)

*Primary Examiner* — Randy Shay
*Assistant Examiner* — Dinah Baria
(74) *Attorney, Agent, or Firm* — Lerner, David, Littenberg, Krumholz & Mentlik, LLP

(57) ABSTRACT

A collapsible prosthetic heart valve includes a stent and a valve assembly. The stent has a proximal end and a distal end and includes a plurality of struts. The struts have free ends configured to inhibit tissue penetration. The valve assembly, including a plurality of leaflets, is disposed within the stent.

5 Claims, 9 Drawing Sheets

(56) References Cited

U.S. PATENT DOCUMENTS

| | | | |
|---|---|---|---|
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,736,845 B2 | 5/2004 | Marquez et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,329,278 B2 | 2/2008 | Seguin et al. | |
| 2003/0144725 A1* | 7/2003 | Lombardi | 623/1.13 |
| 2005/0004583 A1 | 1/2005 | Oz et al. | |
| 2006/0259136 A1 | 11/2006 | Nguyen et al. | |
| 2006/0282157 A1* | 12/2006 | Hill et al. | 623/1.24 |
| 2008/0009940 A1* | 1/2008 | Cribier | 623/2.11 |
| 2008/0071369 A1 | 3/2008 | Tuval et al. | |
| 2008/0147179 A1 | 6/2008 | Cai et al. | |
| 2008/0228264 A1 | 9/2008 | Li et al. | |
| 2008/0269878 A1 | 10/2008 | Iobbi | |
| 2009/0287299 A1* | 11/2009 | Tabor et al. | 623/1.26 |
| 2010/0049313 A1 | 2/2010 | Alon et al. | |
| 2010/0204781 A1 | 8/2010 | Alkhatib | |
| 2010/0249911 A1 | 9/2010 | Alkhatib | |
| 2011/0208298 A1* | 8/2011 | Tuval et al. | 623/2.17 |
| 2012/0197391 A1* | 8/2012 | Alkhatib et al. | 623/2.18 |

OTHER PUBLICATIONS

International Search Report Application No. PCT/US2011/048989, dated Dec. 15, 2011.

International Search Report Application No. PCT/US2011/048967, dated Dec. 15, 2011.

* cited by examiner

BLUNT ENDED STENT FOR PROSTHETIC HEART VALVE

CROSS-REFERENCE TO RELATED APPLICATIONS

This application claims the benefit of the filing date of U.S. Provisional Patent Application No. 61/438,451, filed Feb. 1, 2011, the disclosure of which is hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves that may be repositioned during the deployment procedure.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve assembly or structure mounted on a stent. There are many types of stents. However, two types of stents on which the valve structures are ordinarily mounted include a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implantation site in the patient (e.g., at or near the annulus of the patient's native heart valve), the prosthetic valve can be deployed or released from the delivery apparatus and expanded to the full operating size. For balloon-expandable stents, this generally involves releasing the entire valve, assuring its proper location, and then expanding a balloon positioned within the stent. For self-expanding stents, on the other hand, the stent automatically expands as the sheath covering the valve is withdrawn.

Some of the stents used in constructing collapsible replacement valves may have relatively sharp points or edges at the proximal and/or distal ends. The inventors have found that such sharp points or edges may penetrate into an anatomical feature and/or cause undesirable injury to the surrounding tissue during deployment or redeployment. Indeed, if a collapsible valve is moved from a first deployment location to another location, the likelihood of such injury may increase as a result of unintended tissue penetration and/or undesirable injury.

Therefore, there is a need for further improvements to the devices, systems, and methods for delivery of collapsible prosthetic heart valves, and in particular, self-expanding prosthetic heart valves.

SUMMARY OF THE INVENTION

The present disclosure relates to prosthetic heart valves. In one embodiment, the prosthetic heart valve includes a stent and a valve assembly. The stent and valve assemblies each have a collapsed condition and an expanded condition. The stent and valve assembly also each have a distal end and a proximal end. The stent typically includes a plurality of struts. At least one of the struts of the stent has a free proximal end, free distal end, or both, configured to inhibit tissue penetration. In some embodiments, a plurality of the free proximal ends, free distal ends, or both, is configured to inhibit tissue penetration. In still other embodiments, all of the free proximal ends, free distal ends, or both, of the struts are configured to inhibit tissue penetration. Not including a tissue penetration inhibiting structure at the free end of every strut may be particularly useful in balancing the need for such inhibition with the need to maintain manufacturing simplicity, cost, collapsibility and/or to minimize the size of the collapsed valve for delivery.

In an embodiment of the present invention, a free end of a strut is flattened relative to the cross sectional configuration of the remainder of the strut. In another embodiment, a free end of a strut is smoothly curved. In still another embodiment, a free end of a strut is curled, turned or directed away relative to the general orientation of the strut. In yet another embodiment, a free end of a strut may be generally oval shaped. In other embodiments, a free end of a strut may be semi-spherical. In further embodiments, a free end of a strut may be bulbous or tear-drop shaped and generally thicker in at least one axis relative to the general transverse cross-sectional area of the strut. The bulbous tip of a "bobby" pin provides a suitable analogy.

Any of these shapes or configurations may be used on one or more struts at the proximal and/or distal ends of the stent of the collapsible heart valve so long as it serves the purpose of the invention in retarding tissue penetration or injury during implantation or use. Different shapes or configurations may be used at the distal end than at the proximal end and not every proximal or distal end need be configured to inhibit tissue penetration at all. Moreover, different shapes or configurations of the strut ends may be employed at the same end of the stent. For example, at the proximal end of a collapsible valve in accordance with the invention, every other strut may be smoothly curved while the next adjacent strut contains a relatively flattened end. The ends shaped or configured to inhibit tissue penetration may be further shaped and angled such that they lie generally within the contour of the stent (that portion of the stent to which they are adjacent) or without of that contour. These structures may also generally extend the length of a strut relative to struts that are not configured to inhibit tissue penetration and that length may vary from strut to strut and with the different shapes or configurations used.

According to still another embodiment of the present invention, the free proximal and/or distal ends of first and second adjacent struts are flattened. The first and second struts are joined to one another by a connecting member spaced from the free proximal and/or distal ends so as to define a slot between the respective free proximal and/or distal ends. The free proximal and/or distal ends of the first and second struts and the connecting member collectively define a horseshoe shape. The slot is configured to receive a suture therein.

According to yet another embodiment of the present invention, the free proximal and/or distal ends of the first and second struts have a first length and the slot has a second length of about one-half of the first length. In other embodiments, the ratio of the second length to the first length is between about 0.2 and about 0.6. In some other embodiments of the present invention, the ratio of the second length to the first length is between about 0.6 and about 1.0.

According to an embodiment of the invention, the first and second struts each have a predetermined area in transverse cross-section and the free proximal and/or distal ends of the first and second struts each have a second area in transverse cross-section which is about the same as the predetermined area. In other embodiments, the ratio of the second area to the first area is between about 1 and about 4.

According to still another embodiment of the present invention, first and second adjacent struts may be joined at their proximal and/or distal ends without defining a slot. The joined end of the first and second struts may be configured to inhibit tissue penetration.

BRIEF DESCRIPTION OF THE DRAWINGS

Various embodiments of the present invention are disclosed herein with reference to the drawings, wherein.

DETAILED DESCRIPTION

The reference to "blunted" or "smoothened" ends herein in intended to include all structure configured to inhibit penetration and is not limited to any particular configuration.

As used herein, the term "proximal," when used in connection with a prosthetic heart valve, refers to the end of the heart valve closest to the heart annulus when the heart valve is implanted in a patient, whereas the term "distal," when used in connection with a prosthetic heart valve, refers to the end of the heart valve farthest from the heart annulus when the heart valve is implanted in a patient. For example, when used to replace the aortic valve separating the left ventricle from the aorta, the proximal end of the valve is that portion that will be located in or adjacent the native valve annulus and the distal end will be located in the aorta or aortic sinus.

A collapsible prosthetic heart valve typically includes a stent or frame supporting a valve assembly. Examples of collapsible prosthetic heart valves are described in International Patent Application Publication No. WO/2009/042196; U.S. Pat. No. 7,018,406; U.S. Pat. No. 7,329,278, United States Patent Application Publication Nos. 2005/0113910 and 2009/0030511, the disclosures of all of which are hereby incorporated herein by reference. The valve assembly may be attached to an inner portion of the stent and may include a cuff positioned at the inlet or annulus end of the stent and a plurality of leaflets as is generally known in the art.

Figure 1:
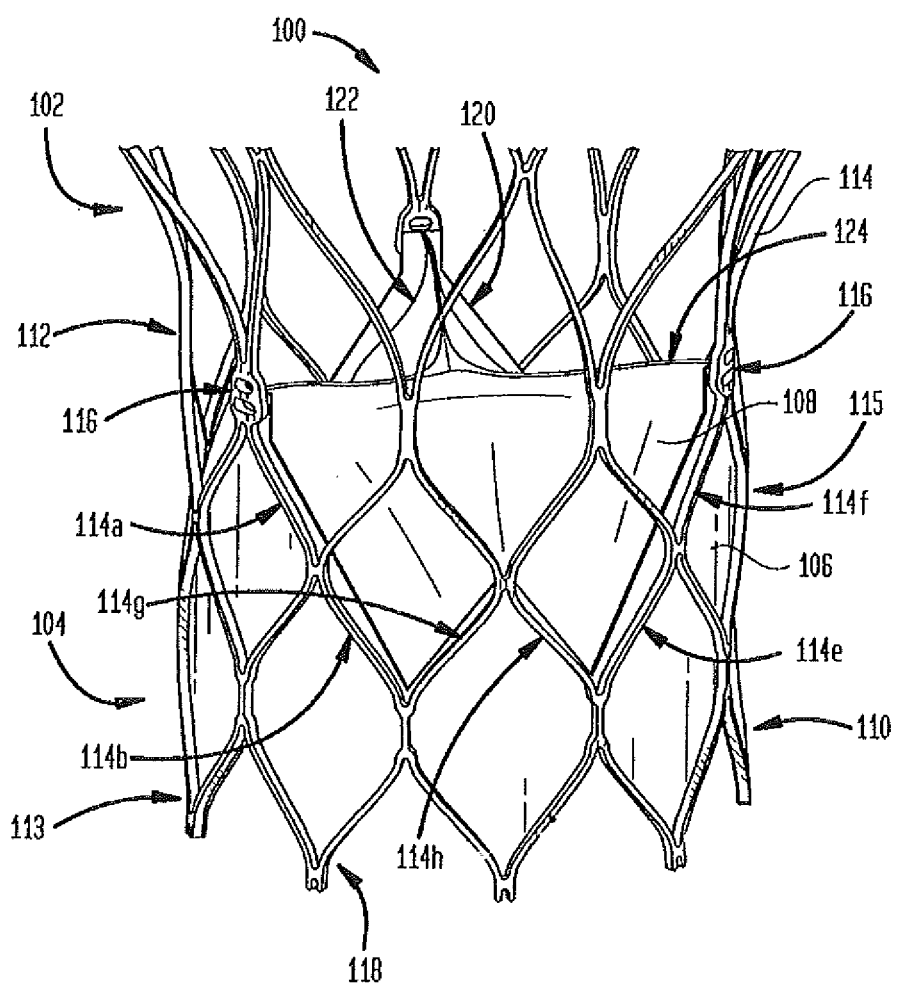
FIG. 1 is a partial side elevational view of a collapsible prosthetic heart valve according to an embodiment of the present invention.

FIG. 1 shows a collapsible prosthetic heart valve 100 according to an embodiment of the present invention. The prosthetic heart valve 100 is designed to replace the function of a native aortic valve of a patient. As discussed in detail below, the prosthetic heart valve 100 has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110 and an aortic section (not shown in this figure). Each of the annulus section 110 and the aortic section of the stent 102 includes a plurality of cells 112 connected to one another around the stent. The annulus section 110 and the aortic section of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure points 116 connecting at least two cells 112 in the longitudinal direction of the stent 102. The commissure points 116 may include eyelets for facilitating the suturing of a valve assembly 104 to the stent 102.

The prosthetic heart valve 100 also includes a valve assembly 104 attached inside the annulus section 110 of the stent 102. United States Patent Application Publication Nos. 2008/0228264, filed Mar. 12, 2007, 2008/0147179, filed Dec. 19, 2007, 2005/0113910, filed Jul. 10, 2004 and 2009/0030511, filed Jan. 29, 2009, the entire disclosures of all of which are hereby incorporated herein by reference, describe suitable valve assemblies. The valve assembly 104 may be wholly or partly formed of any suitable biological material or polymer. Examples of biological materials suitable for the valve assembly 104 include, but are not limited to, porcine or bovine pericardial tissue. Examples of polymers suitable for the valve assembly 104 include, but are not limited to, polyurethane and polyester.

The valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. FIG. 1 shows cuff 106 disposed on the lumenal surface of annulus section 110 so as to cover part of the annulus section while leaving another part thereof uncovered. The valve assembly 104 may further include a plurality of leaflets 108 which collectively function as a one-way valve. The valve assembly may be attached to the stent by suturing, stapling, adhesives or the like as is know in the art. A second or free edge 124 of each leaflet 108 may coapt with the corresponding free edges of the other leaflets, thereby enabling the leaflets to function collectively as a one-way valve.

Irrespective of the attachment means employed, the leaflets 108 may be attached to the stent 102, along at least some struts 114 of the stent 102 to enhance the structural integrity of the valve assembly 104. As a consequence of this attachment, the struts 114 help support the leaflets 108 of the valve assembly 104 and may therefore reduce the strain in the leaflet.

As shown in FIG. 1, at least one leaflet 108 may be attached to the stent 102 so that its first edge 122 is disposed substantially along specific struts 114a, 114b, 114g, 114h, 114e, and 114f located in the annulus section 110 of the stent. That is, the edge 122 is positioned in substantial alignment with struts 114a, 114b, 114g, 114h, 114e, and 114f.

Figure 2:
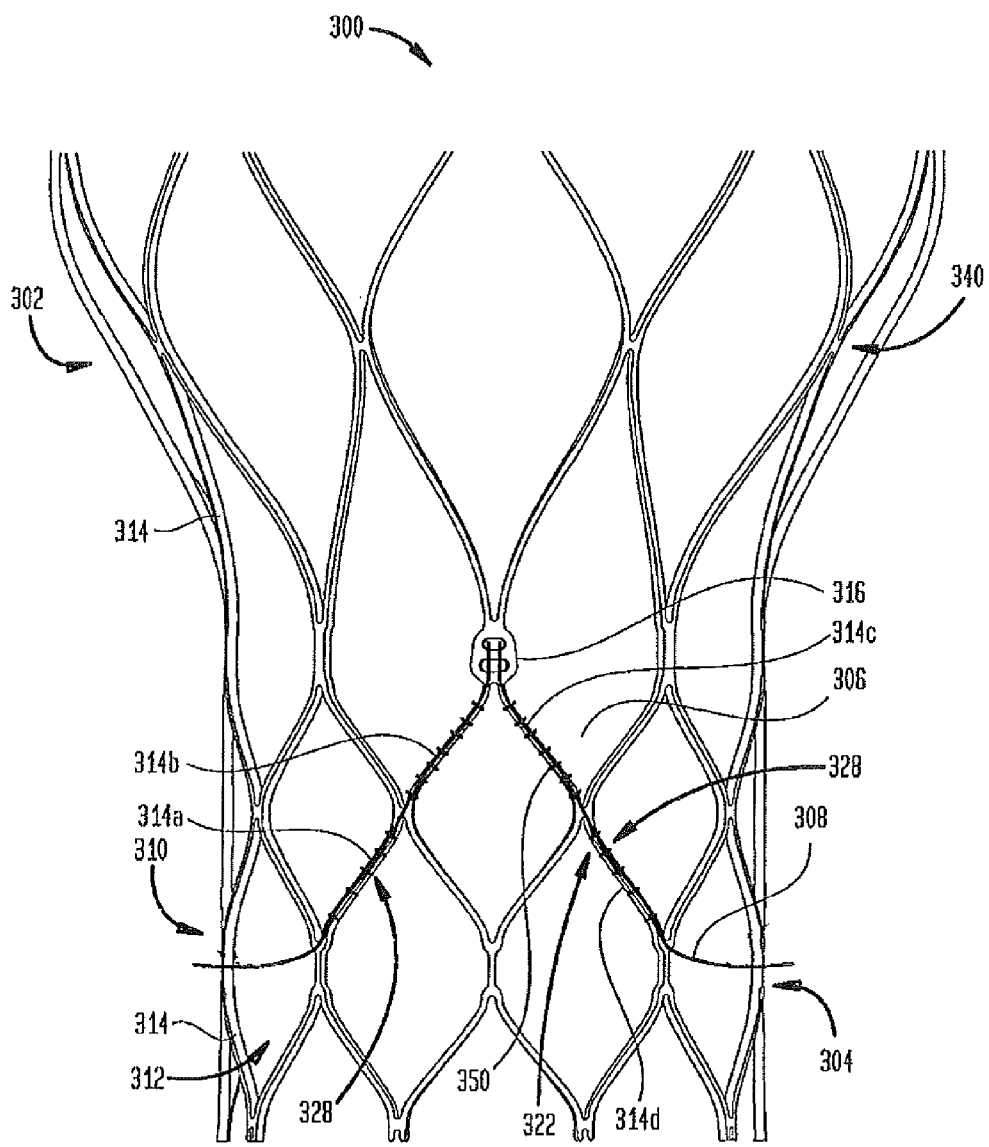
FIG. 2 is a developed view of a portion of a collapsible prosthetic heart valve according to a further embodiment of the present invention in which an edge of the leaflets is disposed substantially along several stent struts.
Figure 3:
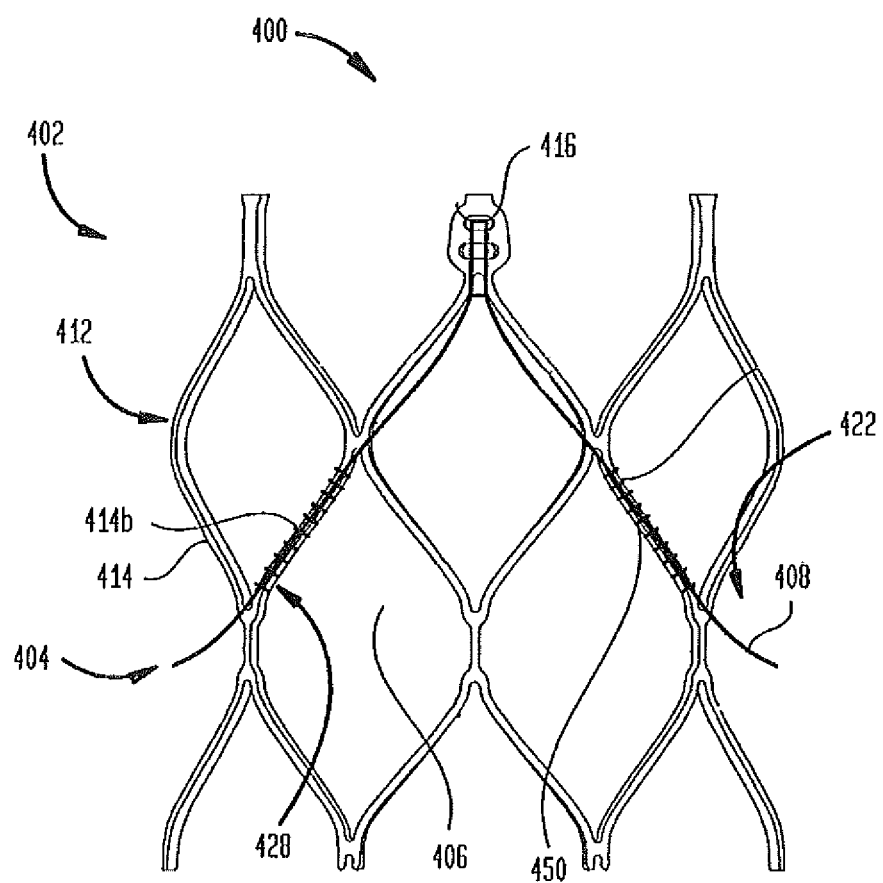
FIG. 3 is a developed view of a portion of a collapsible prosthetic heart valve according to yet another embodiment of the present invention in which some portions of the leaflets of the valve assembly are attached to the stent and disposed substantially along certain stent struts.

As shown in FIGS. 1-3, in one configuration, all of the cells 112 in the bottom annular row 113 of cells 112 may be entirely covered by the cuff 106. The cuff 106 may also entirely cover those cells 112 in the second annular row 115 that are located directly below the commissure points 116. All of the other cells 112 in the stent 102 may be open or not covered by the cuff 106. Hence, there may be no cells 112 which are only partially covered by the cuff 106.

Since the edges of the valve leaflets 108 extend up to the second annular row 115 of cells 112 only in the regions of the commissure points 116, there is little to no likelihood of leakage in the area of the cells between the commissure points in the second annular row of cells, and therefore no need for the cuff 106 to cover this area. This reduction in the area of the cuff 106, both at the proximal end 118 and at the distal end 120 thereof, reduces the amount of material in the valve assembly 104, thereby enabling the prosthetic valve 100 to achieve a smaller cross-section in the collapsed condition.

With reference to FIG. 2, a prosthetic heart valve 300 according to another embodiment of the present invention includes a stent or frame 302, which may be similar to stent 102. The stent 302 may include an aortic section 340 and an annulus section 310. Each of the aortic section 340 and the annulus section 310 may include a plurality of cells 312 connected to one another in one or more annular rows. The cells 312 of the aortic section 340 may be larger than the cells of the annulus section 310. Each cell 312 is formed by a plurality of struts 314. For example, each cell 312 may be formed by four struts 314 and may be substantially diamond-shaped when the stent 302 is in an expanded condition. The stent 302 may further include one or more commissure points 316 for facilitating suturing of a valve assembly 304 to the stent. Each commissure point 316 may interconnect two cells 312 in the same annular row and two cells in different annular rows.

The valve assembly 304 may be attached inside the stent 302, may include a cuff 306 and a plurality of leaflets 308 which collectively function as a one-way valve. The cuff 306 may be located on the inside surface of the stent 302, on the outside surface of the stent, or on both the inside and the outside surfaces. Each leaflet 308 includes an edge 322 attached to the stent 302 and a second free edge 324. An upper portion 328 of the edge 322 may be attached to the stent 302 so as to be disposed substantially along the path of certain struts 314 that lead to the commissure points 316. For example, an upper portion 328 of the edge 322 of at least one leaflet 308 may be attached to, and disposed substantially along, struts 314a and 314b, and an upper portion 328 of the edge 322 of an adjacent leaflet 308 may be attached to and disposed substantially along struts 314c and 314d. The upper portions 328 of the edges 322 of adjacent leaflets 308 may be attached to the commissure point 316 and struts 314a, 314b, 314c, and 314d using sutures 350. Struts 314b and 314c may each have one end attached to a commissure point 316 and each may be part of the same cell 312.

Alternatively, struts 314b and 314c may be attached directly to one another. Struts 314a and 314b may be connected in an end-to-end fashion, and may be part of different cells 312 that are adjacent to one another. Similarly, struts 314c and 314d may be connected in an end-to-end fashion, and may be part of different cells 312 that are adjacent to one another.

With reference to FIG. 3, a collapsible prosthetic heart valve 400 according to an embodiment of the present invention includes a stent 402, which may be similar to stent 102. The stent 402 has collapsed and expanded conditions and includes a plurality of cells 412 connected to one another in annular rows around the stent 402. Each cell 412 is formed by a plurality of struts 414 and may be substantially diamond shaped when the stent 402 is in the expanded condition. For example, one cell 412 may be formed by four interconnected struts 414.

The stent 402 may further include one or more commissure points 416 that interconnect two adjacent cells 412 located in one annular row and two other cells 412 located in the next adjacent rows above and below the one row. The commissure points 416 may facilitate the suturing of a valve assembly 404 to the stent 402.

The valve assembly 404 may include a cuff 406 attached to the interior and/or exterior of the stent 402. In addition to the cuff 406, the valve assembly 404 includes a plurality of leaflets 408 attached to the stent 402 collectively defining a one-way valve. Each leaflet 408 includes a first edge 422 attached to the stent 402 and a second free edge 424. At least one leaflet 408 may be attached to the stent 402 so that the upper portions 428 of its edge 422 are substantially disposed along the path of certain struts 414.

As shown in FIG. 3, one upper portion 428 of the edge 422 of one leaflet 408 may be connected to a commissure point 416 and may be disposed along and connected to a strut 414b spaced from the commissure point.

Any stent described herein may also be used in conjunction with a valve assembly produced from a single piece of tissue, sheet or fabric as described in United States Patent Application Nos. 2005/0013910 and 2009/0030511.

In operation, any of the embodiments of the prosthetic heart valve described above may be used to replace a native heart valve, such as the aortic valve. The prosthetic heart valve may be delivered to the desired site (e.g., near a native valve annulus) using any suitable delivery device known in the art. During delivery, the prosthetic heart valve is disposed inside the delivery device in the collapsed condition. The delivery device may be introduced into a patient using the transfemoral, transapical or transseptal approach. Once the delivery device has reached the target site, the user may deploy any of the prosthetic heart valves described above. Upon deployment, the prosthetic heart valve expands into secure engagement within the native valve annulus. When the prosthetic heart valve is properly positioned inside the heart, it works as a one-way valve, allowing blood to flow in one direction and preventing blood from flowing in the opposite direction.

In each of the prosthetic heart valve embodiments described above, the valve assembly preferably is spaced from the distal or aortic end of the stent by a distance that enables a partial deployment of the heart valve by an amount sufficient for the valve leaflets of the prosthetic valve to operate as intended, while the distal end of the stent remains captured by the delivery device. More particularly, the annulus end of the prosthetic heart valve may be deployed first while the aortic end of the prosthetic heart valve remains at least partially covered by the distal sheath of the delivery device. The annulus portion of the prosthetic heart valve may be deployed so that the entirety of the valve leaflets, up to and including the commissures, is deployed and fully operational. By deploying the prosthetic heart valve in this manner, the user can determine whether the valve is properly positioned relative to the native valve annulus. If the user determines that the positioning of the valve is acceptable, the remainder of the valve may be deployed. However, if it is determined that the position is improper, the user may resheath the valve and either reposition it for redeployment, or remove it entirely from the patient. This can be particularly important in very high risk patients who would typically be recipients of these types of valves, because of the nature of their condition and the impact that may have on the shape and/or condition of the native valve and valve annulus.

Figure 4:
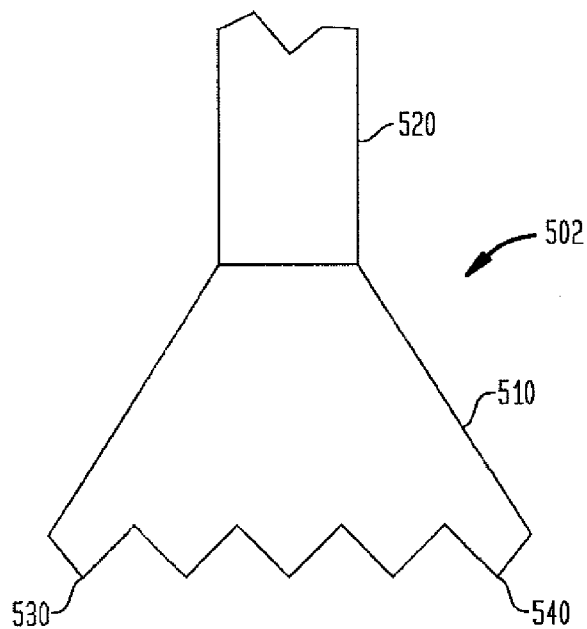
FIG. 4 is a highly schematic diagrammatic view showing a portion of a prosthetic heart valve according to a still further embodiment of the present invention.

While there are many advantages to partial deployment of the valve, depending upon the valve structure, one additional problem may occur during partial deployment, which will be explained with reference to FIG. 4. As the annular section 510 of the stent 502 is unsheathed and partially deployed, the proximal end 530 of the stent (the end to be disposed in or near the native valve annulus) could contact various anatomical features. As schematically illustrated in FIG. 4, if the free proximal end 530 of the stent 502 were to include sharp points 540 or other sharp features, such as edges or corners, they could penetrate into or otherwise damage these anatomical features unintentionally. This could cause undesirable injury and trauma to the area and/or could interfere with partial deployment and redeployment. Furthermore, if it is necessary to resheath and redeploy the stent 502 at another location, the sharp points 540 could penetrate into one or more anatomical features multiple times at multiple locations. Although the description above refers to the proximal end, in some cases the distal end of the valve may be deployed first. In such cases, any sharp points or edges on the distal end of the stent may undesirably penetrate in surrounding tissue.

Therefore, in addition, or instead, it may be desirable to employ structures at the distal end of the strut to inhibit tissue penetration and irritation caused during deployment. Moreover, while following deployment there should be little if any movement, the collapsible valve must withstand significant pressures and forces during the heart's compression. This could, if only slightly, cause, for example, the general movement of the distal end of the valve away from the heart such that it engages the aorta or aortic sinus forcefully. Shifts in the anatomical structures could also cause similar relative movement. The use of penetration inhibiting structures at the distal end, instead of, or in addition to, those used at the proximal end of the stent, may therefore be desirable.

Figure 5A:
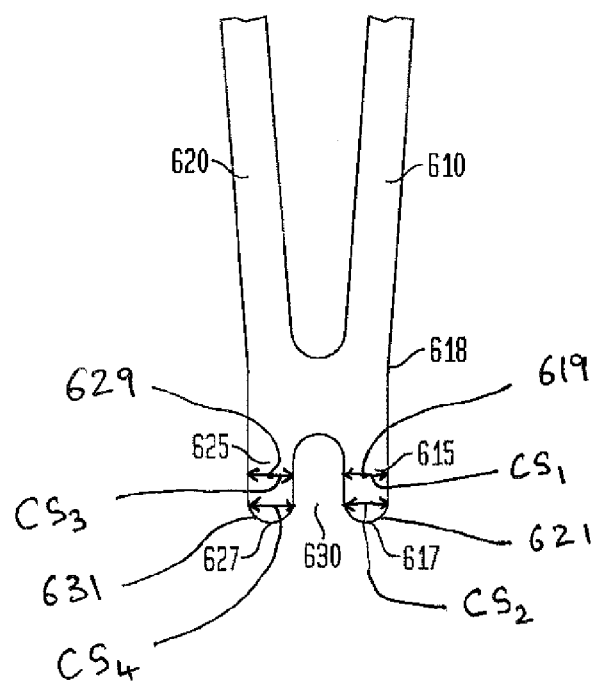
FIGS. 5A-5I are enlarged front views of the free ends of the stent struts according to various embodiments of the present invention.

Accordingly, as shown in FIGS. 5A-5I, some or all of the struts or other structures at the proximal end and/or the distal end of the stent may be sized, shaped, and aligned so as to reduce the risk of unintended penetration and mitigate the risk of tissue damage during the user's assessment of the placement of the partially deployed valve. In other words, the blunted or smoothened ends of the strut may be configured to inhibit tissue penetration. Referring now to FIG. 5A, first and second adjacent struts 610, 620 are illustrated. Each strut 610, 620 has a free proximal end 615, 625, respectively. According to an exemplary embodiment, free proximal ends 615, 625 have proximal-most points 617, 627, which are located along respective smoothly curved end surfaces, that, are less likely to penetrate into an anatomical feature or cause an injury thereto. The struts 610 and 620 are joined to one another by a connector 618 spaced from the proximal-most points 617, 627. The free proximal ends 615 and 625, and the connector 618 collectively define a "horseshoe" shape around a slot 630. The slot 630 may receive a suture (not shown). The slot 630 may be used to suture the cuff and/or the leaflets to the stent. The free proximal ends 615, 625 have has a midpoint between the connector 618 and the proximal-most point 617, 627 and a first cross-section at the midpoint. All points between the midpoint and the proximal-most point 617, 627 have a cross-section, for example, second cross-section, which is equal to or smaller than the first cross-section.

Figure 5B:
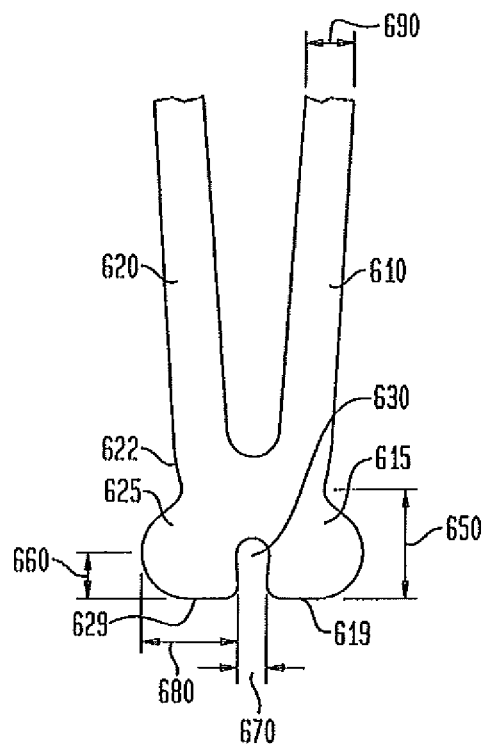

Now referring to FIG. 5B, two adjacent struts 610, 620 have respective free proximal ends 615, 625. In the illustrated embodiment, free proximal ends 615, 625 have generally rounded or bulbous portions 618, 628, respectively, and generally flattened ends 619, 629, respectively. The "flattened" ends 619, 629 are flattened relative to the rounded or bulbous portions 618, 628 and may have a generally horizontal surface as seen in FIG. 5B. Thus, the portions 618, 628 are generally smoothly curved. Due to the flattened ends 619, 629 and the bulbous portions 618, 628, any force exerted by the free proximal ends 615, 625 on an anatomical feature is likely to be distributed over a larger area and, thus, less likely to implant therein or cause injury thereto. The struts 610 and 620 are joined to one another by a connector 622 spaced from the flattened ends 619, 629. The free proximal ends 615 and 625, and connector 622 collectively define a "horseshoe" shape around a slot 630.

The slot 630 has a length 660 and a transverse width 670. The free proximal ends 615, 625 have a length 650 and a transverse width 680. In an exemplary configuration, the ratio of the length 660 of the slot 630 to the length 650 of the free proximal ends 615, 625 may range from about 0.2 to about 0.6. In an exemplary embodiment, the ratio of the transverse width 670 to the transverse width 680 may be between about 0.2 and about 1.0. The slot 630 may receive a suture (not shown). The transverse cross-section area of the rounded or bulbous sections 618, 628 may range from about one to about four times the transverse cross-section of struts 610, 620. The transverse cross-section of struts 610, 620 may be based on a transverse dimension 690, for example, a diameter of the struts 610 and 620 in case of generally circular struts 610 and 620. Of course, in case of other shapes of the struts 610 and 620, the transverse dimension 690 may take a different form.

Figure 5C:
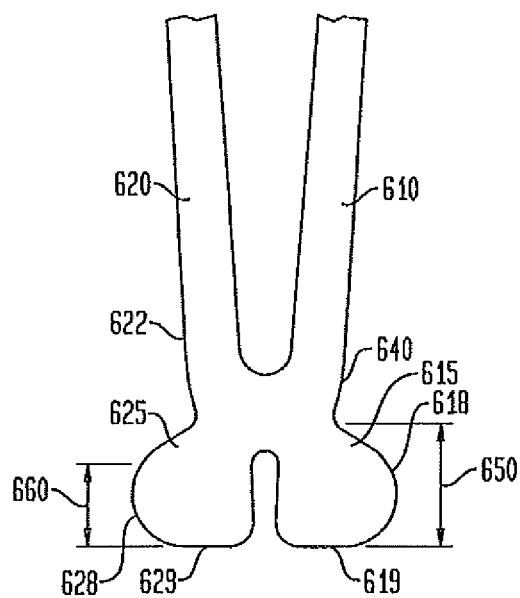

FIG. 5C illustrates yet another embodiment of the free proximal ends 615, 625. The free proximal ends 615, 625 are joined to one another by a connector 622. Collectively, the free proximal ends 615 and 625, and connector 622 define a "horseshoe" shape around a slot 640. In an exemplary embodiment, the ratio of the length 660 of the slot 640 to the length 650 of the free proximal ends 615, 625 may range from about 0.6 to about 1.0. The slot 640 may receive a suture (not shown).

Figure 5D:
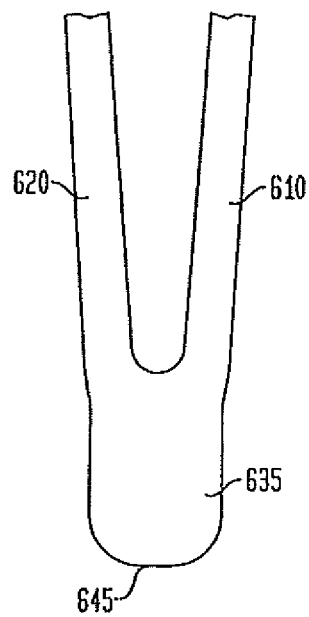

FIG. 5D illustrates still another embodiment of the blunted end for a strut. First and second adjacent struts 610, 620 may be joined to form a common end 635. The common end 635 may have a rounded end 645. The embodiment of FIG. 5D is similar to the embodiment of FIG. 5A, except that there is no slot 630. In yet another embodiment, instead of a slot, a hole 685 could be provided at rounded end 645 through which a suture could be threaded, as illustrated in FIG. 5H.

Figure 5E:
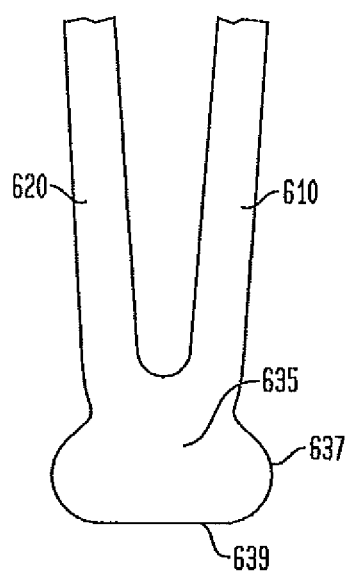

Referring now to FIG. 5E, an embodiment includes first and second adjacent struts 610, 620 culminating at a common end 635. The common end 635 is generally similar to the ends 615, 625 of FIG. 6B, except that there is no slot 630 in this embodiment. The common end 635 has a rounded or bulbous portion 637 and a generally flattened end 639. In yet another embodiment, instead of a slot, a hole 685 could be provided at rounded end 645 through which a suture could be threaded, as illustrated in FIG. 5I.

Figure 5F:
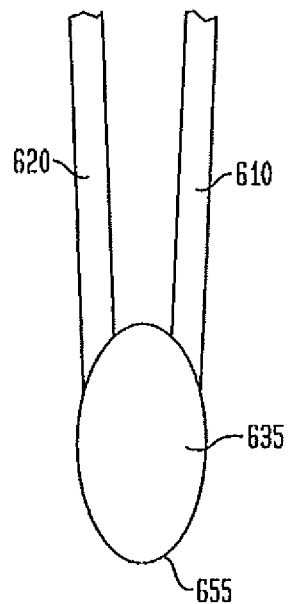
Figure 5G:
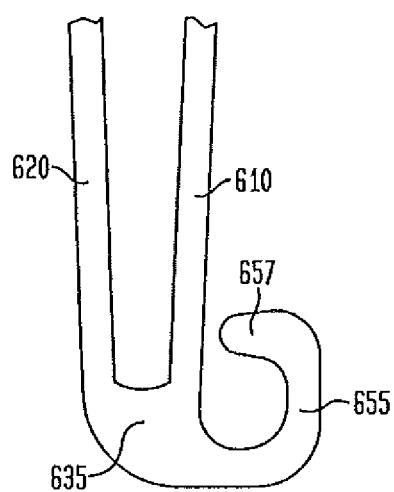
Figure 5H:
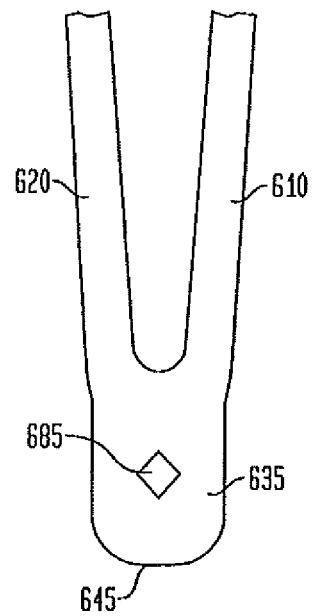
Figure 5I:
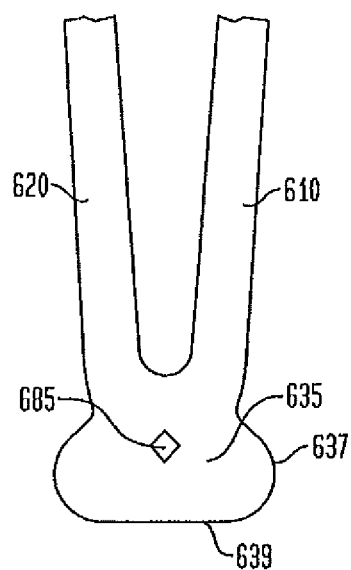

FIG. 5F illustrates another embodiment of the common end 635. The common end 635 may take the form of an oval configuration 655. FIG. 5G illustrates yet another embodiment of the common end 635. The common end 635 extends in a generally hook shaped configuration defined by a generally vertical segment 655 followed by a generally inwardly directed horizontal segment 657. Although the illustrated common end 635 extends generally along the circumferential contour of the stent, other embodiments may have the common end extending radially inward or outward from the stent.

Of course, other shapes for the free proximal ends 615, 625 which will inhibit unwanted penetration or other damage are also contemplated. For example, in one configuration, the free proximal ends 615, 625 may have rounded ends (such as 617, 627 of FIG. 5A) as well as rounded or bulbous portions (such as 618, 628 of FIG. 5B). In yet another configuration, the free proximal ends 615, 625 may have a generally semi-spherical shape. Desirably, both the shape and size of the free proximal ends 615, 625 may be configured to help distribute any pressure that may be exerted in a localized area during partial deployment so as to resist penetration. In further embodiments, a free end of a strut may be bulbous or tear-drop shaped and generally thicker in at least one axis relative to the general transverse cross-sectional area of the strut, for example, a drop of polymer coagulated at the end of the strut.

Also, whether surfaces are rounded as shown in FIG. 5A, or a mixture of rounded and blunted surfaces as shown in FIGS. 5B and 5C, and whether they continue the contour of the annulus section 110 of the stent or are angled slightly in or out of the contour to further limit their contact with anatomical features, the result is likely be a lower chance of damage to surrounding tissue during partial deployment without interfering with the ability to function and be resheathed and repositioned as needed. Still further, various shapes of the free proximal ends 615, 625 may be combined with different lengths 660 of the slots 630, 640, depending on the requirements of a given application, without departing from the scope of the invention.

Figure 6A:
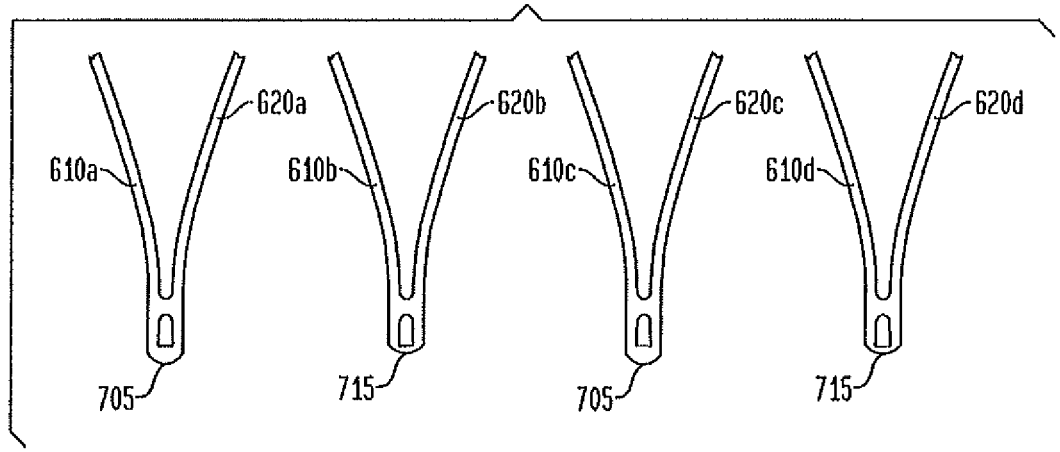
FIG. 6A is an enlarged partial diagrammatic view of the struts of the stent according to an embodiment of the present invention.
Figure 6B:
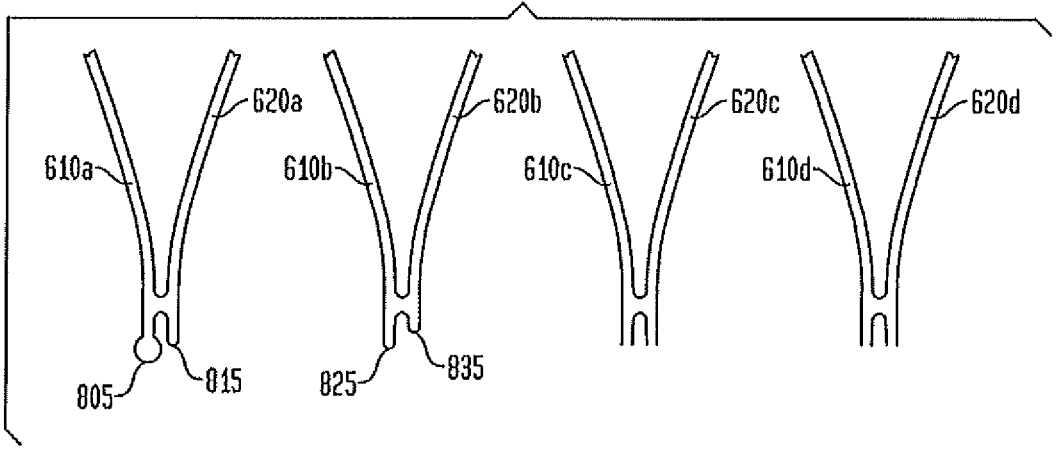
FIG. 6B is an enlarged partial diagrammatic view of the struts of the stent according to another embodiment of the present invention.

Referring now to FIGS. 6A-6B, a stent may have different blunted or smoothened ends for different struts. For example, in FIG. 6A, first pair of struts 610a, 620a has a first type of blunted end 705 whereas second pair of struts 610b, 620b has a second type of blunted end 715. Likewise, third pair of struts 610c, 620c has the first type of blunted end 705 whereas fourth pair of struts 610d, 620d has the second type of blunted end 715. It is to be noted that blunted ends 705 and 715 are only schematic representations and may include any type of blunted ends including, not limited to, those illustrated in FIGS. 5A 5I. Thus, a single stent may be different types of blunted or smoothened ends. In an embodiment of the invention illustrated in FIG. 6B, a single pair of struts 610a, 620a have two different types of blunted or smoothened ends as schematically represented by 805, 815 while another pair of struts 610b, 620b have two different types of blunted or smoothened ends as schematically represented by 825, 835. Other pairs of struts 610c, 620c and 610d, 620d may include any types of blunted or smoothened ends, without being specifically illustrated in FIG. 6B. It will further be understood that only some of the struts of a stent may have blunted or smoothened ends, for example, every alternate pair of struts or every third pair of struts. Various other combinations of the blunted or smoothened ends of the struts of a given stent, not specifically described, are also considered to be within the scope of the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
   a collapsible and expandable stent having a proximal end and a distal end, the stent comprising a plurality of struts having free proximal ends configured to inhibit tissue penetration, each of the free proximal ends having proximal-most point; and
   a collapsible and expandable valve assembly disposed within the stent, the valve assembly including a plurality of leaflets;
   wherein first and second ones of the plurality of struts are joined to one another by a connecting member spaced from the proximal-most point so as to define a slot between the free proximal ends, each of the free proximal ends having a midpoint between the connecting member and the proximal-most point a first cross-section at the midpoint such that all points of the free proximal ends between the midpoint and the proximal-most point have a cross-section equal to or smaller than the first cross-section.

2. The prosthetic heart valve according to claim 1, wherein the free proximal ends of the struts have a smoothly curved end surface.

3. The prosthetic heart valve according to claim 1, wherein the free proximal ends of the first and second struts and the connecting member collectively define a horseshoe shape.

4. The prosthetic heart valve according to claim 1, wherein the slot is configured to receive a suture therein.

5. The prosthetic heart valve according to claim 1, wherein an annulus section of the stent has a curved, circumferential contour, and the free proximal ends of the struts have at least one surface which continues the contour.

* * * * *